United States Patent [19]
Minagawa et al.

[11] Patent Number: 5,096,710
[45] Date of Patent: Mar. 17, 1992

[54] POISON BAIT FOR CONTROL OF NOXIOUS INSECTS

[75] Inventors: Fumiyasu Minagawa, Toyonaka; Takuji Kohama, Osaka; Hitoshi Kawada, Ibaraki; Goro Shinjo, Toyonaka; Kazuyuki Maeda, Nishinomiya, all of Japan

[73] Assignee: Sumitomo Chemical Company, Limited, Japan

[21] Appl. No.: 527,780

[22] Filed: May 24, 1990

[30] Foreign Application Priority Data

May 27, 1989 [JP] Japan .................. 1-133323

[51] Int. Cl.$^5$ .............. A01N 25/08; A01N 25/12; A01N 25/34; C08B 37/16
[52] U.S. Cl. ................. 424/405; 424/408; 424/409; 424/410; 424/538; 424/DIG. 10; 424/DIG. 11; 514/778; 536/103
[58] Field of Search ............. 424/405, 408, 409, 410

[56] References Cited

FOREIGN PATENT DOCUMENTS

| | | |
|---|---|---|
| 1-143806 | 6/1989 | Japan . |
| 2-067203 | 3/1990 | Japan . |
| 2-067204 | 3/1990 | Japan . |
| 63218604 | 5/1990 | Japan . |

OTHER PUBLICATIONS

Remington's Pharmaceutical Sciences, Gennaro et al., 18th Ed., p. 1321.

*Primary Examiner*—Thurman K. Page
*Assistant Examiner*—Carlos Azpuru

[57] ABSTRACT

A bait composition in a tablet form, which comprises as the essential components (a) at least one insect-growth controlling agent chosen from (a-1) insect juvenile hormone-like compounds and (a-2) insect chitin-synthesis inhibitors, (b) dextrin and (c) a plant oil in an amount of not more than 10% by weight to the total bait composition.

35 Claims, No Drawings

POISON BAIT FOR CONTROL OF NOXIOUS INSECTS

The present invention pertains to a poison bait for control of noxious insects.

There have heretofore been commercially available some powdery poison baits for exterminating noxious insects such as cockroaches. These conventional poison baits in a powdery form are, however, practically disadvantageous and dangerous in causing many problems from the standpoints of sanitary and daily usages. For instance, they attach to the hands on handling, fly about the surroundings after being situated in desired places or are apt to be erroneously taken as food by infants and household pets.

In order to solve the above problems, a poison bait in a tablet form was put into the market, which comprises boric acid as the active ingredient. For assurance of the eradicating effect, however, such poison bait tablets should contain boric acid in such a large amount as about 20 to about 30% by weight. Because of this reason, they are still not safe for infants and household pets. In fact, it is reported that even a baby powder containing boric acid in an amount of only 5% by weight accidentally produced the death of an infant (11th Japan Pharmacopoeia Commentary, C-1475 (1986)). In addition, the bait containing boric acid makes cockroaches suffer from diarrhea and produce soft excrements, so that their habitats and surroundings are considerably stained thereby.

There are also known some poison baits in tablets, which comprise as the active ingredient an insecticide chosen from organic phosphorus insecticides, and carbamate insecticides, etc. However, said insecticides have each a characteristic odor, and a tablet preparation comprising the same is apt to be repelled by cockroaches. Thus, the feeding attractant effect is much inferior, and naturally the eradicating effect is lowered. Further, these insecticides easily hydrolyze even with a slightest amount of water to produce a certain specific odor, whereby the feeding attractant effect is deteriorated and the eradicating effect is decreased. Said hydrolysis results in lowering of the content of the active ingredient itself, and the insecticidal effect is thus remarkably deteriorated.

A proposal was made to provide a poison bait composition in a tablet form which comprises at least one insect-growth controlling agent chosen from insect juvenile hormone-like compounds and insect chitin-synthesis inhibitors, and crystalline cellulose (JP-A-01-143806). However, incorporation of feeding attractants having an excellent effect such as animal powders and crushed biscuit into said composition tends to cause cracking of the resultant tablet, and tabletting is made impossible unless the feeding attractant is used in a finely pulverized state. Due to the above reason, the feeding attractant as usable is restricted to starches or sugars, and therefore the effect is not satisfactory.

There has thus been a great demand for a poison bait safe for human beings as well as domestic animals, a remarkable feeding attractant effect and a sufficient insecticidal effect in addition to the safety on handling and the stability of the active ingredient.

As a result of extensive study, it has now been found that a tabletted poison bait composition comprising a certain specific insect-growth controlling agent in combination with some certain additives meets the above demand.

According to this invention, there is provided a poison bait composition in a tablet form, which comprises as the essential components (a) at least one insect-growth controlling agent chosen from (a-1) insect juvenile hormone-like compounds and (a-2) insect chitin-synthesis inhibitors, (b) dextrin and (c) a plant oil in an amount of not more than 10% by weight to the total bait composition, optionally with (d) at least one feeding attractant chosen from (d-1) sugars in an amount of not more than 60% by weight, (d-2) cereal flours in an amount of not more than 50% by weight, (d-3) crushed biscuit in an amount of not more than 50% by weight and (d-4) animal powders in an amount of not more than 10% by weight to the total bait composition.

The bait composition comprising the above components can be stably formulated into a tablet and exerts a sufficient eradicating effect against harmful insects. The composition is also effective in inhibiting emergence of insects as well as reducing reproductivity. Further, incorporation of sugars, cereal flours, crushed biscuit and/or animal powders as the additional components enhance the feeding attractant effect and the stability of the essential components.

As the component (a-1), there are exemplified dodecadienoate compounds, oxim ether compounds, pyridyl ether compounds, carbamate compounds, etc., of which representative compounds are shown in Table 1:

TABLE 1

| Generic name or code | Chemical name |
|---|---|
| Methoprene | Isopropyl (2E-4E)-11-methoxy-3,7,11-trimethyl-2,4-dodecadienoate |
| Hydroprene | Ethyl (2E-4E)-3,7,11-trimethyldodeca-2,4-dienoate |
| Pyriproxyfen | 2-[1-Methyl-2-(4-phenoxyphenoxy)ethoxy]pyridine |
| S-21149 | Propionaldehyde oxime O-2-(4-phenoxypheoxy)ethyl ether |
| S-21150 | Propionaldehyde oxime O-2-(4-phenoxypheoxy)propyl ether |
| Fenoxycarb | O-Ethyl N-[2-(4-phenoxyphenoxy)ethyl]carbamate |
| R-20458 | 1-(4-Ethylphenoxy)-6,7-epoxy-3,7-dimethyl-2-octene |

As the component (a-2), benzoylphenyl urea compounds may be used, of which examples are shown in Table 2:

TABLE 2

| Generic name or code | Chemical name |
|---|---|
| Diflubenzuron | 1-(4-Chlorophenyl)-3-(2,6-difluorobenzoyl)-urea |
| Triflumuron | 2-Chloro-N-[[[4-(trifluoromethoxy)phenyl]amino]carbonyl]benzamide |
| EL 494 | N-[[[5-(4-Bromophenyl)-6-methyl-2-pyradinyl]amino]carbonyl]-2,6-dichlorobenzamide |
| Teflubenzuron | 1-(3,5-Dichloro-2,4-difluorophenyl)-3-(2,6-difluorobenzoyl)urea |
| Chlorfluazuron | 1-[3,5-Dichloro-4-(3-chloro-5-trifluoromethyl-2-pyridyloxy)phenyl]-3-(2,6-difluorobenzoyl)urea |
| XRD-473 | N-[[[3,5-Dichloro-4-(1,1,2,2-tetrafluoroethoxy)phenyl]amino]carbonyl]-2,6-difluorobenzamide |
| S-71624 | N-2,6-Difluorobenzoyl-N'-[2-fluoro-4-(1,1,2,2-tetrafluoroethoxy)phenyl]urea |
| S-71622 | N-2,6-Difluorobenzoyl-N'-(2-fluoro-4-tri- |

TABLE 2-continued

| Generic name or code | Chemical name |
|---|---|
| | fluoromethylphenyl)urea |

The components (a-1) and (a-2) as exemplified above may include their geometric isomers and optical isomers.

The amount of the insect-growth controlling agent (a) varies depending on the kind of the compound used and the target insect. Normally, however, the component (a) may be contained in an amount of about 0.01 of about 2% by weight to the total composition.

Dextrin as the component (b) includes a hydrolyzed product of starch powders (e.g. potato, sweet potato, corn, wheat, rice) with an acid, heat or amylase. It is normally used in an amount of about 10 to about 99% by weight to the total weight of the bait composition.

Specific examples of the plant oils as the component (c) are soybean oil, rapeseed oil, sesame oil, wheat germ oil, etc. The amount to be used may be not more than 10% by weight to the total composition.

In addition to the above essential components, the bait composition may comprise optionally at least one feeding attractant chosen from (d-1) sugars, (d-2) cereal flours, (d-3) crushed biscuit and (d-4) animal powders as the component (d). As the sugars, there may be exemplified sucrose, glucose, fructose, lactose, black sugar, brown sugar, soft brown sugar, etc., among which black sugar, brown sugar and soft brown sugar are particularly preferred. The sugars are normally used in an amount of 0 to about 60% by weight to the total composition.

The cereal flours as the component (d-2) may be, for instance, potato powders, sweet potato powders, corn powders, wheat flours, rice powders, corn flours, etc., the amount of which may be, for instance, 0 to about 50% by weight. The crushed biscuit (d-3) may be any of the commercial products on the market and is used in an amount of 0 to about 50% by weight. Examples of the animal powders as the component (d-4) are fish powders, chrysalis powders, Euphauciasea powders, shrimp powders, etc. These may be used in an amount of 0 to about 10% by weight of the total composition.

When desired, the bait composition may further comprise an additive(s) and/or an auxiliary agent(s), particularly an anti-oxidizing agent, a preservative, a mis-feeding inhibitor, a flavoring agent, a filler, etc. Examples of the anti-oxidizing agent are erythorbic acid, sodium erythorbate, dibutyl hydroxytoluene, dl-alphatocopherol, nordihydroguaiaretic acid, methylhydroxyanisole, propyl gallate, guaiac resin, L-cysteine hydrochloride, etc. Examples of the preservative are benzoic acid, sodium benzoate, salicylic acid, diphenyl, sorbic acid, potassium sorbate, dehydroacetic acid, sodium dehydroacetate, isobutyl p-oxybenzoate, isopropyl p-oxybenzoate, ethyl p-oxybenzoate, butyl p-oxybenzoate, propyl p-oxybenzoate, calcium propionate, sodium propionate, etc. As the mis-feeding inhibitor, there may be exemplified red pepper powders, Amaranth, Amaranth aluminium lake, Erythrosine, Erythrosine aluminium lake, New Coccine, Phloxine, Rose Bengal, Acid Red, Tartrazine, Tartrazine aluminium lake, Sunset Yellow FCF, Sunset Yellow FCF aluminium lake, Fast Green FCF, Fast Green FCF aluminium lake, Brilliant Blue FCF, Brilliant Blue FCF aluminium lake, Indigo Carmine, Indigo Carmine aluminium lake, beta-carotene, copper chlorophyll, etc. Examples of the flavoring agent are cheese flavor, butter flavor, peanut flavor, peach flavor, strawberry flavor, milk flavor, etc. As the filler, there may be used calcium silicate, diatomaceous earth, crystalline cellulose, clay, kaolin, talc, bentonite, zeolite, sepiolite, attapulgite, etc.

For preparation of the poison bait composition of the invention, the essential and optional components as above mentioned may be mixed together to make a uniform mixture, which is then subjected to tabletting by a per se conventional procedure. For instance, one or more insect-growth controlling agents are mixed with dextrin, plant oil and a feeding attractant to make a uniform mixture, which is then tabletted by a per se conventional procedure to give a bait composition in a tablet of desired size normally under a pressure of about 10 to about 500 kg/cm$^2$.

The thus obtained bait composition exerts a remarkable insecticidal effect against a wide range of harmful insects, of which examples are cockroaches (Blattidae) such as American cockroach (*Periplaneta americana*), German cockroach (*Blattella germanica*) and smoky-brown cockroach (*Periplaneta fuliginosa*, ants (Formicidae) such as Monomorium sp. and *Formica japonica*, deathwatch and drugstore beetles (Anobiidae) such as cigarette beete (*Lasioderma serricorne*) and biscuit beetle (*Stegobium paniceum*), darkling beetles (Tenebrionidae) such as red flour beetle (*Tribolium castaneum*) and confused flour beetle (*Tribolium confusum*) and cucujid beetles (Cucujidae) such as saw-toothed grain beetle (*Oryzaephilus surinamensis*) and flat grain beetle (*Cryprolestes pusillus*), termites (Isoptera) such as Formosan subterranean termite (*Coptotermes formosanus*) and *Reticulitermes speratus*, etc.

Practical embodiments for preparation of the insecticidal composition according to the invention are illustratively shown in the following Examples wherein % are by weight unless otherwise indicated.

EXAMPLES 1 to 6

Pyriproxyfen (0.05%), dextrin (96.85% in Example 1; 30.0% in Examples 2 to 6) and dehydroacetic acid (0.1%) were mixed together, and an essential oil, sugar, cereal flours, crushed biscuit and animal powders as shown in Table 3 were incorporated therein, followed by mixing uniformly. The resultant mixture was tableted under a compression of 15 kg/cm$^2$ to make tablets, each weighing about 4 g (diameter, about 30 mm).

The thus obtained tablets as a bait were subjected to evaluation of the tablettability, stability of the active ingredient, the feeding attractant effect, the inhibitory effect on emergence and the inhibitory effect on reproduction according to the following procedures, and the results are shown in Table 3:

1) Tabletability:

Observation was made immediately after the tableting under a compression of 15 kg/cm$^2$ and also after 10 days storage at 50° C., and the tabletability of a tablet of about 4 g (diameter, 30 mm) was evaluated with respect to production of cracking: (O) no crack; (X) cracks.

2) Stability of the active ingredient:

The bait in a tablet form was kept at 50° C. for 10 days and subjected to measurement of the residual percent of the active ingredient by gas chromatography. Evaluation was made on the following criteria:

| Criteria | Residual active ingredient |
|---|---|
| ++ | >80 % |
| + | 70-80% |
| − | <70% |

3) Feeding attractant effect (i.e., effect of attracting and stimulating the insects to eat food):

Fifty imagos of *Blattella germanica* (even numbers of males and females) were admitted in a container having a bottom area of 0.12 m$^2$ where the bait in a tablet form as well as a solid bait as control were placed. The attractant rate was calculated on the basis of the numbers of insects attracted by the bait within a designated period, and classified according to the following criteria:

| Criteria | Attractant rate |
|---|---|
| ++ | >80% |
| + | 70-80% |
| − | <70% |

4) Inhibitory effect on emergence:

Ten last instar larvae of *Blattella germanica* (even numbers of males and females) were admitted in a container having a bottom area of 100 cm$^2$ where the bait in a tablet form as well as a solid bait as control were placed, and observation was made on the failure of emergence, abnormality of wings, and supernumerary molting over a period of three weeks. The number of failures in emergence, abnormality of wings, and supernumerary molting was counted to calculate the emergence inhibitory rate and the results are classified according to the following criteria:

| Criteria | Emergence inhibitory rate |
|---|---|
| ++ | >80% |
| + | 70-80% |
| − | <70% |

5) Inhibitory effect on reproduction:

Ten last instar larvae of *Blattella germanica* (even numbers of males and females) were admitted in a container having a bottom area of 100 cm$^2$ where the bait in a tablet form as well as a solid bait as comparison were placed, and the number of hatched eggs and the rate of emergence were observed over a period of four weeks. Reduction in the number of the next generation in contrast to the untreated group was calculated and the results were classified according to the following criteria:

| Criteria | Reduction in the next generation |
|---|---|
| ++ | >80% |
| + | 70-80% |
| − | <70% |

TABLE 3

| | | Example 1 | Example 2 | Example 3 | Example 4 | Example 5 | Example 6 |
|---|---|---|---|---|---|---|---|
| Composition (%) | Pyriproxyfen | 0.05 | 0.05 | 0.05 | 0.05 | 0.05 | 0.05 |
| | Dextrin | 96.85 | 30.0 | 30.0 | 30.0 | 30.0 | 30.0 |
| | Dehydroacetic acid | 0.1 | 0.1 | 0.1 | 0.1 | 0.1 | 0.1 |
| Plant oil | Sesame oil | 3.0 | 2.0 | 2.0 | 2.0 | 2.0 | 5.0 |
| | Corn oil | — | — | 5.0 | — | — | — |
| Sugar | Black sugar | — | — | 20.0 | — | — | 10.0 |
| | Brown sugar | — | — | — | 50.0 | — | — |
| | Soft brown sugar | — | — | — | — | 10.0 | — |
| Starch powder | Potato starch | — | 50.0 | 33.0 | 10.0 | 7.85 | — |
| | Crushed biscuit | — | — | — | — | 50.0 | 40.0 |
| Animal powder | Euphausiacea powder | — | 2.5 | — | — | — | 5.0 |
| | Chrysalis powder | — | 2.5 | — | — | — | 5.0 |
| | Calcium silicate | — | 12.85 | 9.85 | 7.85 | — | 4.85 |
| Evaluation | Tabletability A*1) | O | O | O | O | O | O |
| | B*2) | O | O | O | O | O | O |
| | Stability of active ingredient | ++ | ++ | ++ | ++ | ++ | ++ |
| | Feeding attractant effect A | ++ | ++ | ++ | ++ | ++ | ++ |
| | B | ++ | ++ | ++ | ++ | ++ | ++ |
| | Emergence inhibitory effect A | ++ | ++ | ++ | ++ | ++ | ++ |
| | B | ++ | ++ | ++ | ++ | ++ | ++ |
| | Reproduction control effect A | ++ | ++ | ++ | ++ | ++ | ++ |
| | B | ++ | ++ | ++ | ++ | ++ | ++ |

Note:
*1) immediately after tableting.
*2) after being kept at 50° C. for 10 days.

EXAMPLES 7 to 9

In the same manner as in Examples 1 to 6, there were prepared tablets as a bait comprising the components as shown in Table 4. The thus obtained tablets were subjected to evaluation of various properties in the same manner as in Examples 1 to 6, the results of which are also shown in Table 4.

COMPARATIVE EXAMPLES 1 to 3

In the same manner as in Examples 7 to 9 but not using sesame oil, there were prepared tablets as a bait and evaluation of these baits was made in the same manner as in Examples 7 to 9. The results are also shown in Table 4.

TABLE 4

| | | Example 1 | Example 2 | Example 3 | Comparative 1 | Comparative 2 | Comparative 3 |
|---|---|---|---|---|---|---|---|
| Composition (%) | Hydroprene | 0.5 | — | — | 0.5 | — | — |
| | S-21149 | — | 0.30 | — | — | 0.30 | — |
| | Teflubenzuron | — | — | 0.70 | — | — | 0.70 |
| | Dextrin | 50.0 | 50.0 | 50.0 | 50.0 | 50.0 | 50.0 |
| | Sesame oil | 2.0 | 2.0 | 2.0 | — | — | — |
| | Black sugar | 10.0 | 10.0 | 10.0 | 10.0 | 10.0 | 10.0 |
| | Crushed biscuit | 32.5 | 32.7 | 32.3 | 34.5 | 34.7 | 34.3 |

TABLE 4-continued

|  |  | Example | | | Comparative | | |
| --- | --- | --- | --- | --- | --- | --- | --- |
|  |  | 1 | 2 | 3 | 1 | 2 | 3 |
| Animal powder | Euphausiacea powder | 2.5 | 2.5 | 2.5 | 2.5 | 2.5 | 2.5 |
|  | Chrysalis powder | 2.5 | 2.5 | 2.5 | 2.5 | 2.5 | 2.5 |
| Evaluation | Tabletability A*1) | ○ | ○ | ○ | ○ | ○ | ○ |
|  | B*2) | ○ | ○ | ○ | ○ | ○ | ○ |
|  | Stability of active ingredient | ++ | ++ | ++ | + | + | + |
|  | Feeding attractant A | ++ | ++ | ++ | ++ | ++ | ++ |
|  | B | ++ | ++ | ++ | + | + | + |
| Emergence inhibitory effect | A | ++ | ++ | ++ | ++ | ++ | ++ |
|  | B | ++ | ++ | ++ | − | − | − |
| Reproduction control effect | A | ++ | ++ | ++ | ++ | ++ | ++ |
|  | B | ++ | ++ | ++ | − | − | − |

Note:
*1) immediately after tableting.
*2) after being kept at 50° C. for 10 days.

As understood from the above test results, the bait composition containing no essential oil such as sesame oil is inferior in various properties.

Examples 10 to 16

In the same manner as in Examples 1 to 6, there were prepared tablets comprising the essential components (e.g., insect-growth controlling compound, dextrin, essential oil) and optional or auxiliary components (e.g., sugars, crushed biscuit, animal powders, mis-food inhibitor, flavoring agent, filler, preservatives) as shown in Table 5. Various properties of these tablets were evaluated and also shown in Table 5, from which it is understood that all of these tablets exhibit excellent properties and no crack or damage is produced on tabletting.

TABLE 5

|  |  |  | Example | | | | | | |
| --- | --- | --- | --- | --- | --- | --- | --- | --- | --- |
|  |  |  | 10 | 11 | 12 | 13 | 14 | 15 | 16 |
| Composition (%) | Pyriproxyfen |  | 0.05 | — | — | — | — | — | — |
|  | Hydroprene |  | — | 0.5 | — | — | — | — | — |
|  | Fenoxycarb |  | — | — | 0.1 | — | — | — | — |
|  | Diflubenzuron |  | — | — | — | 1.0 | — | — | — |
|  | S-71624 |  | — | — | — | — | 0.5 | — | — |
|  | Chlorfluazuron |  | — | — | — | — | — | 0.5 | — |
|  | S-71622 |  | — | — | — | — | — | — | 0.05 |
|  | Dextrin |  | 72.85 | 57.4 | 37.0 | 97.0 | 52.4 | 67.4 | 67.85 |
|  | Potato starch |  | — | — | — | — | — | — | — |
|  | Plant oil | Sesame oil | 2.0 | 2.0 | — | — | 2.0 | 2.0 | 2.0 |
|  |  | Corn oil | — | — | 2.0 | 2.0 | — | — | — |
|  | Sugar | Black sugar | 20.0 | — | — | — | 20.0 | 10.0 | 10.0 |
|  |  | Brown sugar | — | 20.0 | — | — | — | — | — |
|  |  | Soft brown sugar | — | — | 20.0 | — | — | — | — |
|  | Crushed biscuit |  | — | 20.0 | 20.0 | — | 20.0 | 10.0 | 10.0 |
|  | Animal powder | Euphausiacea powder | 2.5 | — | 5.0 | — | 2.5 | 10.0 | 10.0 |
|  |  | Chrysalis powder | 2.5 | — | 5.0 | — | 2.5 | — | — |
|  | Red pepper powder |  | — | — | 0.5 | — | — | — | — |
|  | Red pigment No. 1 |  | — | — | — | — | trace | trace | trace |
|  | Butter flavoring agent |  | — | — | 0.3 | — | — | — | — |
|  | Calcium silicate |  | — | — | 10.0 | — | — | — | — |
|  | Dehydroacetic acid |  | 0.1 | 0.1 | 0.1 | — | 0.1 | 0.1 | 0.1 |
| Evaluation | Tabletability A*1) |  | ○ | ○ | ○ | ○ | ○ | ○ | ○ |
|  | B*2) |  | ○ | ○ | ○ | ○ | ○ | ○ | ○ |
|  | Stability of active ingredient |  | ++ | ++ | ++ | ++ | ++ | ++ | ++ |
|  | Feeding attractant effect | A | ++ | ++ | ++ | ++ | ++ | ++ | ++ |
|  |  | B | ++ | ++ | ++ | ++ | ++ | ++ | ++ |
|  | Emergence inhibitory effect | A | ++ | ++ | ++ | ++ | ++ | ++ | ++ |
|  |  | B | ++ | ++ | ++ | ++ | ++ | ++ | ++ |
|  | Reproduction control effect | A | ++ | ++ | ++ | ++ | ++ | ++ | ++ |
|  |  | B | ++ | ++ | ++ | ++ | ++ | ++ | ++ |

Note:
*1) immediately after tableting.
*2) after being kept at 50° C. for 10 days.

COMPARATIVE EXAMPLES 4 to 10

In the same manner as in Examples 10 to 16 but using potato starch instead of dextrin, there were prepared tablets as shown in Table 7. Various properties of these tablets were observed in the same manner as in Examples 10 to 16, and the results are also shown in Table 7. It was specifically noticeable that the tablets thus formulated had many cracks or damages during formulation due to poor stability. The feeding attractant effect, emergence inhibitory effect and production control effect were reduced.

TABLE 7

|  |  | Comparative Example | | | | | | |
| --- | --- | --- | --- | --- | --- | --- | --- | --- |
|  |  | 4 | 5 | 6 | 7 | 8 | 9 | 10 |
| Composition (%) | Pyriproxyfen | 0.05 | — | — | — | — | — | — |
|  | Hydroprene | — | 0.5 | — | — | — | — | — |
|  | Fenoxycarb | — | — | 0.1 | — | — | — | — |
|  | Diflubenzuron | — | — | — | 1.0 | — | — | — |
|  | S-71624 | — | — | — | — | 0.5 | — | — |
|  | Chlorfluazuron | — | — | — | — | — | 0.5 | — |
|  | S-71622 | — | — | — | — | — | — | 0.05 |
|  | Dextrin | — | — | — | — | — | — | — |
|  | Potato starch | 72.85 | 57.4 | 37.0 | 97.0 | 52.4 | 67.4 | 67.85 |
|  | Plant Oil — Sesame oil | 2.0 | 2.0 | — | — | 2.0 | 2.0 | 2.0 |
|  | Corn oil | — | — | 2.0 | 2.0 | — | — | — |
|  | Sugar — Black sugar | 20.0 | — | — | — | 20.0 | 10.0 | 10.0 |
|  | Brown sugar | — | 20.0 | — | — | — | — | — |
|  | Soft brown sugar | — | — | 20.0 | — | — | — | — |
|  | Crushed biscuit | — | 20.0 | 20.0 | — | 20.0 | 10.0 | 10.0 |
|  | Animal powder — Euphausiacea powder | 2.5 | — | 5.0 | — | 2.5 | 10.0 | 10.0 |
|  | Chrysalis powder | 2.5 | — | 5.0 | — | 2.5 | — | — |
|  | Red pepper powder | — | — | 0.5 | — | — | — | — |
|  | Red pigment No. 1 | — | — | — | — | trace | trace | trace |
|  | Butter flavoring agent | — | — | 0.3 | — | — | — | — |
|  | Calcium silicate | — | — | 10.0 | — | — | — | — |
|  | Dehydroacetic acid | 0.1 | 0.1 | 0.1 | — | 0.1 | 0.1 | 0.1 |
| Evaluation | Tabletability A*1) | X | X | X | X | X | X | X |
|  | B*2) | X | X | X | X | X | X | X |
|  | Stability of active ingredient | ++ | ++ | ++ | ++ | ++ | ++ | ++ |
|  | Feeding attractant effect A | + | ++ | ++ | + | ++ | + | + |
|  | B | + | + | + | + | + | + | + |
|  | Emergence inhibitory effect A | + | ++ | ++ | + | ++ | + | + |
|  | B | + | + | + | + | + | + | + |
|  | Reproduction control effect A | + | ++ | ++ | + | ++ | + | + |
|  | B | + | + | + | + | + | + | + |

Note:
*1)immediately after tableting.
*2)after being kept at 50° C. for 10 days.

It is understood from the above results that the tablets according to the present invention are quite satisfactory in stability, feeding attractant effect, emergence inhibitory effect and reproduction control effect. Further, since no cracks or damage occurs during tabletting, the composition of the present invention is useful as a bait for harmful insects such as cockroaches.

What is claimed is:

1. A bait composition in a tablet form, which comprises as the essential components (a) at least one insect-growth controlling agent chosen from (a-1) insect juvenile hormone-like compounds and (a-2) insect chitin-synthesis inhibitors in an amount of from about 0.01 to about 2% by weight of the total bait composition, (b) dextrin in an amount of from about 10 to about 99% by weight of the total bait composition, and (c) a plant oil in an amount of not more than 10% by weight of the total bait composition.

2. The composition according to claim 1, which further comprises (d) at least one feeding attractant selected from the group consisting of (d-1) sugars in an amount of not more than 60% by weight, (d-2) cereal flours in an amount of not more than 50% by weight, (d-3) crushed biscuit in an amount of not more than 50% by weight and (d-4) animal powders in an amount of not more than 10% by weight of the total bait composition.

3. A method for controlling noxious insects, which comprises applying the bait composition according to claim 1 to the area inhabited by said noxious insects.

4. The method according to claim 3, wherein said noxious insects are selected from the group consisting of Blattidae, Formicidae, Anobiidae, Tenebrionidae, Cucujidae, and Isoptera.

5. A process for preparing a poison bait composition in a tablet form, which comprises uniformly mixing as the essential components (a) at least one insect-growth controlling agent chosen from (a-1) insect juvenile hormone-like compounds and (a-2) insect chitin-synthesis inhibitors, (b) dextrin and (c) a plant oil in an amount of not more than 10% by weight of the total bait composition, optionally with any additional component(s), and tabletting the mixture in a tablet form of desired size.

6. The composition according to claim 1, wherein said insect juvenile hormone-like compound is selected from the group consisting of dodecadienoate compounds, oxim ether compounds, pyridyl ether compounds, and carbamate compounds.

7. The method according to claim 3, wherein said insect juvenile hormone-like compound is selected from the group consisting of dodecadienoate compounds, oxim ether compounds, pyridyl ether compounds, and carbamate compounds.

8. The process according to claim 5, wherein said insect juvenile hormone-like compound is selected from the group consisting of dodecadienoate compounds, oxim ether compounds, pyridyl ether compounds, and carbamate compounds.

9. The bait composition according to claim 6, wherein said insect juvenile hormone-like compound is selected from the group consisting of isopropyl (2E-4E)-11-methoxy-3,7,11-trimethyl-2,4-dodecadienoate, ethyl (2E-4E)-3,7,11-trimethyldodeca-2,4-dienoate, 2-pyridine, propionaldehyde oxime 0-2-(4-pheonxypheoxy)ethyl ether, propionaldehyde oxime 0-2-(4-phenoxypheoxy)propyl ether, 0-Ethyl N-carbamate, 1-(4-Ethylphenoxy)-6,7-epoxy-3,7-dimethyl-2-octene, and geometric and optical isomers thereof.

10. The method according to claim 7, wherein said insect juvenile hormone-like compound is selected from the group consisting of isopropyl (2E-4E)-11-methoxy-3,7,11-trimethyl-2,4-dodecadienoate, ethyl (2E-4E)-3,7,11-trimethyldodeca-2,4-dienoate, 2-pyridine, propionaldehyde oxime 0-2-(4-phenoxypheoxy)ethyl ether, propionaldehyde oxime 0-2-(4-phenoxypheoxy)propyl ether, 0-Ethyl N-carbamate, 1-(4-Ethylpheonxy)-6,7-epoxy-3,7-dimethyl-2-octene, and geometric and optical isomers thereof.

11. The process according to claim 8, wherein said insect juvenile hormone-like compound is selected from the group consisting of isopropyl (2E-4E)-11-methoxy-3,7,11-trimethyl-2,4-dodecadienoate, ethyl (2E-4E)-3,7,11-trimethyldodeca-2,4-dienoate, 2-pyridine, propionaldehyde oxime 0-2-(4-phenoxypheoxy)ethyl ether, propionaldehyde oxime 0-2-(4-phenoxypheoxy)propyl ether, 0-Ethyle N-carbamate, 1-(4-Ethylphenoxy)-6,7-epoxy-3,7-dimethyl-2-octene, and geometric and optical isomers thereof.

12. The composition according to claim 1, wherein said insect chitin-synthesis inhibitor is a benzoylphenyl urea compound.

13. The method according to claim 3, wherein said insect chitin-synthesis inhibitor is a benzoylphenyl urea compound.

14. The process according to claim 5, wherein said insect chitin-synthesis inhibitor is a benzoylphenyl urea compound.

15. The composition according to claim 12, wherein said benzoylphenyl urea compound is selected from the group consisting of 1-(4-Chlorophenyl)-3-(2,6-difluorobenzoyl)urea, 2-Chloro-N-benzamide, N-2,6-dichlorobenzamide, 1-(3,5-Dichloro-2,4-difluorophenyl)-3-(2,6-difluorobenzoyl)urea, 1-3-(2,6-difluorobenzoyl)urea, N-2,6-difluorobenzamide, N-2,6-Difluorobenzoyl-N'-urea, N-2,6-Difluorobenzoyl-N'-(2fluoro-4-trifluoromethylphenyl)urea, and geometric and optical isomers thereof.

16. The method according to claim 13, wherein said benzoylphenyl urea compound is selected from the group consisting of 1-(4-Chlorophenyl)-3-(2,6-diufluorobenzoyl)urea, 2-Chloro-N-benzamide, N-2,6-dichlorobenzamide, 1-(3,5-Dichloro-2,4-difluorophenyl)-3-(2,6-difluorobenzoyl)urea, 1-3-(2,6-difluorobenzoyl)urea, N-2,6-difluorobenzamide, N-2,6-Difluorobenzoyl-N'-urea,N-2,6-Difluorobenzoyl-N'-(2-fluoro-4-trifluoromethylphenyl)urea, and geometric and optical isomers thereof.

17. The process according to claim 14, wherein said benzoylphenyl urea compound is selected from the group consisting of 1-(4-Chlorophenyl)-3-(2,6-difluorobenzoyl)urea, 2-Chloro-N-benzamide, N-2,6-dichlorobenzamide, 1-(3,5-Dichloro-2,4-difluorophenyl)-3-(2,6-difluorobenzoyl)urea, 1-3-(2,6-difluorobenzoyl)urea, N-2,6-difluorobenzamide, N-2,6-Difluorobenzoyl-N'-urea, N-2,6-Difluorobenzoyl-N'-(2-fluoro-4-trifluoromethylphenyl)urea, and geometric and optical isomers thereof.

18. The method according to claim 3, wherein said insect-growth controlling agent is present in an amount of from about 0.01 to about 2% by weight of the total composition.

19. The process according to claim 5, wherein said insect-growth controlling agent is present in an amount of from about 0.01 to about 2% by weight of the total composition.

20. The composition according to claim 1, wherein said plant oil is selected from the group consisting of soybean oil, rapeseed oil, sesame oil, and wheat germ oil.

21. The method according to claim 3, wherein said plant oil is selected from the group consisting of soybean oil, rapeseed oil, sesame oil, and wheat germ oil.

22. The process according to claim 5, wherein said plant oil is selected from the group consisting of soybean oil, rapeseed oil, sesame oil, and wheat germ oil.

23. The composition according to claim 2, wherein said sugars are selected from the group consisting of sucrose, glucose, fructose, lactose, black sugar, brown sugar, and soft brown sugar.

24. The composition according to claim 23, wherein said sugars are selected from the group consisting of black sugar, brown sugar, and soft brown sugar.

25. The composition according to claim 2, wherein said cereal flours are selected from the group consisting of potato powder, sweet potato powders, corn powders, wheat powders, wheat flours, rice powders, and corn flours.

26. The composition according to claim 2, wherein said animal powders are selected from the group consisting of fish powders, chrysalis powders, Euphauciasea powders and shrimp powders.

27. The composition according to claim 1, further comprising an additive or an auxiliary agent.

28. The composition according to claim 27, wherein said auxiliary agent is selected from the group consisting of an anti-oxidizing agent, a preservative, a mis-feeding inhibitor, a flavoring agent, and a filler.

29. The composition according to claim 28, wherein said anti-oxidizing agent is selected from the group consisting erythorbic acid, sodium erythorbate, dibutyl hydroxytoluene, dl-alpha-tocopherol, nordihydroguaiaretic acid, methylhydroxyanisole, propyl gallate, guaiac resin, and L-cysteine hydrochloride.

30. The composition according to claim 28, wherein said preservative is selected from the group consisting of benzoic acid, sodium benzoate, salicylic acid, diphenyl, sorbic acid, potassium sorbate, dehydroacetic acid, sodium dehydroacetate, isobutyl p-oxygenzoate, isopropyl p-oxybenzoate, ethyl p-oxybenzoate, butyl p-oxybenzoate, propyl p-oxybenzoate, calcium propionate, and sodium propionate.

31. The composition according to claim 28, wherein said mis-feeding inhibitor is selected from the group consisting of red pepper powders, Amaranth, Amaranth aluminium lake, Erythrosine, Erythrosine aluminium lake, New Coccine, Phloxine, Rose Bengal, Acid Red, Tartrazine, Tartrazine aluminiumm lake, Sunset Yellow FCF, Sunset Yellow FCF aluminium lake, Fast Green FCF, Fast Green FCF aluminium lake, Brilliant Blue FCF, Brilliant Blue FCF aluminium lake, Indigo Carmine, Indigo Carmine aluminium lake, beta-carotene, and copper chlorophyll.

32. The composition according to claim 28, wherein said flavoring agent is selected from the group consisting of cheese flavor, butter flavor, peanut flavor, peach flavor, strawberry flavor, and milk flavor.

33. The composition according to claim 28, wherein said filler is selected from the group consisting of calcium silicate, diatomaceous earth, crystalline cellulose, clay, kaolin, talc, bentonite, zeolite, sepiolite, and attapulgite.

34. The process according to claim 5, wherein said tabletting is conducted under a pressure of about 10 to about 500 kg/cm$^2$.

35. The bait composition according to claim 1, comprising 0.05% by weight 2-pyridine, 30.0 to 96.85% by weight dextrin, 0.1% dehydroacetic acid, an essential oil, sugar, cereal flours, crushed biscuit, and animal powders, tabletted under a compression of 15 kg/cm$^2$.

* * * * *